US012653994B2

(12) United States Patent
Ettori et al.

(10) Patent No.: US 12,653,994 B2
(45) Date of Patent: Jun. 16, 2026

(54) MICRONEEDLE ARRAY, ACTUATOR AND METHOD OF USE

(71) Applicant: Ares Trading S.A., Aubonne (CH)

(72) Inventors: Maxime Ettori, Eysins (CH); Craig Nelson, Melbourn (GB); Michael Noble, Melbourn (GB); John Somerville, Melbourn (GB)

(73) Assignee: Ares Trading S.A., Aubonne (CH)

( * ) Notice: Subject to any disclaimer, the term of this patent is extended or adjusted under 35 U.S.C. 154(b) by 936 days.

(21) Appl. No.: 17/782,201

(22) PCT Filed: Dec. 20, 2019

(86) PCT No.: PCT/EP2019/086853
§ 371 (c)(1),
(2) Date: Jun. 3, 2022

(87) PCT Pub. No.: WO2021/121638
PCT Pub. Date: Jun. 24, 2021

(65) Prior Publication Data
US 2023/0024124 A1     Jan. 26, 2023

(51) Int. Cl.
*A61M 37/00*          (2006.01)
(52) U.S. Cl.
CPC . *A61M 37/0015* (2013.01); *A61M 2037/0023* (2013.01); *A61M 2037/0046* (2013.01); *A61M 2037/0061* (2013.01); *A61M 2205/103* (2013.01); *A61M 2205/3653* (2013.01); *A61M 2209/088* (2013.01)
(58) Field of Classification Search
CPC ...... A61M 37/0015; A61M 2037/0023; A61M 2037/0046; A61M 2037/0061; A61M 2205/103

USPC .......................................................... 604/22
See application file for complete search history.

(56) References Cited

U.S. PATENT DOCUMENTS

| | | | |
|---|---|---|---|
| 2006/0094985 A1* | 5/2006 | Aceti | A61B 5/681 604/113 |
| 2007/0100255 A1 | 5/2007 | Boecker et al. | |
| 2011/0264048 A1 | 10/2011 | O'dea et al. | |
| 2015/0273148 A1 | 10/2015 | Sexton et al. | |

(Continued)

FOREIGN PATENT DOCUMENTS

| | | |
|---|---|---|
| CN | 104941060 A | 9/2015 |
| KR | 100893250 B1 | 4/2009 |
| WO | 03066128 A2 | 8/2003 |

(Continued)

OTHER PUBLICATIONS

English translation of Notice of Reasons for Rejection for Japanese application No. 2022-537227, Oct. 31, 2023, 6 pages.

(Continued)

*Primary Examiner* — Phillip A Gray
(74) *Attorney, Agent, or Firm* — Carter, DeLuca & Farrell LLP

(57) ABSTRACT

Transdermal drug delivery devices are described herein such as a microneedle array patch, to be placed on the skin for transdermal delivery of a medicament. The transdermal drug delivery device for delivery of a bioactive agent through mammalian skin comprises an array of microneedles and a means to actuate the microneedles, wherein the actuation means actuates the microneedles separately.

20 Claims, 5 Drawing Sheets

(56) References Cited

U.S. PATENT DOCUMENTS

2018/0353740 A1    12/2018  Cabiri et al.
2019/0111241 A1     4/2019  Arora

FOREIGN PATENT DOCUMENTS

WO        2010022252  A2    2/2010
WO        2013058879  A2    4/2013

OTHER PUBLICATIONS

Machine translation of Chinese Office Action for application No. 201980103171.8, Nov. 18, 2023, 13 pages.

International Search Report and Written Opinion of the International Searching Authority dated Sep. 22, 2020, corresponding to counterpart International Application No. PCT/EP2019/086853; 16 total pages.

English translation of Notice of Reasons for Rejection for Japanese application No. 2022-537227, Jul. 9, 2024, 7 pages.

European search report received for European Patent Application No. 19835416.9, mailing date Jul. 17, 2025.

\* cited by examiner

MICRONEEDLE ARRAY, ACTUATOR AND METHOD OF USE

FIELD

This invention relates transdermal drug delivery devices. In particular, the invention relates to microneedle arrays, such as a microneedle array patch, to be placed on the skin for transdermal delivery of a medicament.

BACKGROUND

Pharmaceutical compositions can be administered through various routes, including for example oral administration or through subcutaneous injection. For certain active ingredients in pharmaceutical compositions a more localized administration is preferred, this is particularly true for larger active ingredients such as for example biologics. Such larger active ingredients are therefore often administered through injection, whether subcutaneous, intramuscular or intravenously.

Examples of active pharmaceutical ingredients that are being administered through injection are for example certain hormonal treatments as in the fertility therapeutic area, insulin, or many of the biologics in the oncology and autoimmune therapeutic areas, such as for example antibody or fusion protein treatments.

Injection administration frequently requires assistance of a trained health care provider or requires patient training. Many patients perceive injection as a painful and cumbersome procedure and in some instances would either forego, stop or infrequently inject with the active pharmaceutical ingredient. As a result, adherence to a treatment plan can be seriously compromised. In addition, the use of an injection device with an exposed needle carries the risk of needle stick injuries which risk from a safety perspective should be minimized as much as possible.

Microneedle technology incorporated as an array in a transdermal patch has provided an attractive alternative to the more convention methods of injection administration. A typical microneedle array for transdermal administration is in the form of a patch which is applied onto the skin of a patient. The pharmaceutical composition including the active pharmaceutical ingredient is delivered to the patient through the array of microneedles, which microneedles are either coated with the pharmaceutical composition or are in part dissolvable, constructed with the solid pharmaceutical composition. Once the active pharmaceutical ingredient is administered through the transdermal patch with microneedle array such transdermal patch can be removed.

Conventional transdermal patches therefore deliver the active pharmaceutical ingredient in a single administration, which could be either as an immediate release composition or an extended release composition. A drawback of such transdermal patches is that they have been designed for single dosing. Certain treatments however require multiple administrations of the active pharmaceutical ingredient over a period of time at preset intervals. For example, certain treatments require once a day injection over for example a two-week period. While removing a transdermal patch at the end of each administration and replacing it with another transdermal patch prior to a subsequent administration is possible it remains very inconvenient to the patient and does not improve the potential for the patient to fail to adhere to a treatment plan.

Accordingly, there is a need for providing a convenient and easy to use device for administering injectable active pharmaceutical ingredients to a patient, particularly wherein the treatment consists of multiple administrations to be delivered over a period of time at preset time intervals.

SUMMARY OF THE INVENTION

The present invention relates to a device for transdermal delivery of an active pharmaceutical ingredient. The device of the present invention is convenient and easy to use for administration to a patient of a treatment with an active pharmaceutical ingredient, which treatment requires multiple administrations over a period of time at preset time intervals. The transdermal microneedle array patch device of the present invention comprises an actuator mechanism for individually addressing one or more microneedles within the array. As a result, a single microneedle array transdermal patch device can be used for multiple administrations over a period of time. Therefore, the device of the present invention provides solutions to the technical problem(s) discussed above in allowing the actuation of one or more individual needles within the microneedle array, thereby allowing for a microneedle array patch device that can be used for multiple administrations over a period of time according to a particular dosing regimen for an active pharmaceutical ingredient. In addition, such device greatly enhances the convenience to patients, particularly in self-administration of the patient at home and increase the potential for adherence to a preset dosing regimen.

In one embodiment of the present invention there is provided a device for delivery of an active pharmaceutical ingredient, a bioactive agent, through mammalian skin comprising an array of microneedles and a means to actuate the microneedles, wherein the actuation means actuates the microneedles separately. In a preferred embodiment the actuation means actuates of a subset of the array of microneedles at the same time. In some embodiments of the present invention the microneedles comprise a dissolvable portion which contains the active pharmaceutical ingredient or composition comprising the active pharmaceutical ingredient.

In an embodiment of the present invention there is provided a device for delivery of a bioactive agent through mammalian skin comprising an array of microneedles and a means to actuate the microneedles, wherein the actuation means actuates the microneedles separately and comprises one or more heating elements and a thermally expandable working medium.

In another embodiment of the present invention there is provided a device for delivery of a bioactive agent through mammalian skin comprising an array of microneedles and a means to actuate the microneedles, wherein the actuation means actuates the microneedles separately and comprises an actuator and a spring on a disc with a spiral-like guiding track.

In another embodiment of the present invention there is provided a method of administering a bioactive agent to a mammal using a device for delivery of a bioactive agent through mammalian skin comprising an array of microneedles and a means to actuate the microneedles, wherein the actuation means actuates the microneedles separately.

Further objects and advantageous features of the invention will be apparent from the claims, from the detailed description, and annexed drawings.

DETAILED DESCRIPTION OF THE
INVENTION

The devices and methods described herein are, in one aspect, directed to transdermal devices, including an intra-epidermal delivery device for administering an active pharmaceutical ingredient to a patient. In one exemplary embodiment the systems and methods provide delivery devices for administering an active pharmaceutical ingredient into or below the stratum corneum of the skin of a patient. As used herein, transdermal refers to the exchange of a substance, such as an active pharmaceutical ingredient (a biological agent) or a vaccine, through one or more layers of skin.

The devices and methods are particularly suitable for use in administering various active pharmaceutical agents/ingredients (bioactive agents), to a patient, and notably to a human patient. An active pharmaceutical agent/ingredient includes a substance having biological activity that can be delivered through the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, adjuvants, biologics, and the like. Other substances which can be delivered intradermally to a patient include proteins, peptides and fragments thereof. The proteins and peptides can be naturally occurring, synthesized or recombinantly produced. Suitable examples of active pharmaceutical agents/ingredients include insulin or fertility hormones, such as recombinant gonadotropins (for example recombinant human FSH).

The microneedle array device for transdermal delivery as described herein is advantageous in that it provides a convenient and easy to use device for the transdermal administration of an active pharmaceutical agent. It is also convenient to the patient that the device described herein can be used in a treatment requiring multiple administrations over a period of time at certain preset times within this period. The patient does not need to replace a microneedle device or inject multiple times, each time with a different device, during the course of the treatment. As such the device and its use in a method of treatment also improves the adherence of the patient to such treatment regime.

In certain embodiments of the device a communication module is included. The communication module can be any communication module that is capable of transferring data from the device to a central server/external server. The transferred data relates to one or more of confirmation of activation of the microneedle array, number of needles being activated, time and date of activation of the microneedle array, or change in number of microneedles to be activated as part of a dose adjustment. The communication module can use any number of connections to transfer data including for example wireless connectivity.

Figure 1:
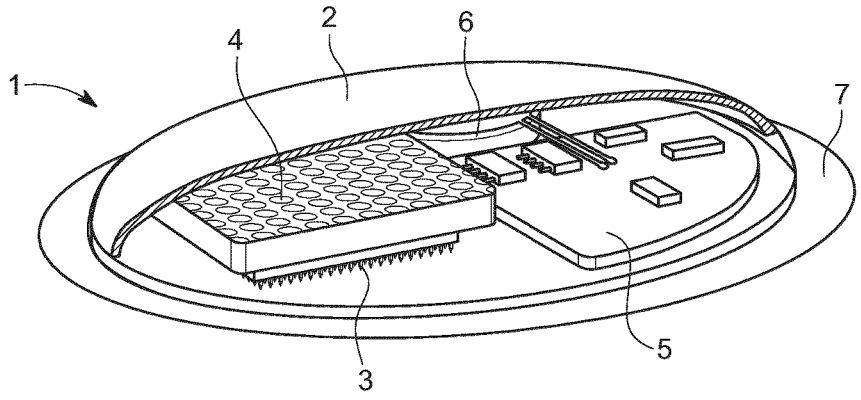
FIG. 1 shows a cut-out top view of a transdermal patch with microneedle array including an actuation mechanism.

FIG. 1 depicts in general an embodiment of the device for delivery of a bioactive agent through mammalian skin comprising an array of microneedles and a means to actuate the microneedles, wherein the actuation means actuates the microneedles separately. In FIG. 1, the device (1) is a transdermal patch device, i.e. a device that is to be adhered to the skin of a patient (an on-skin device) encompassing a mechanism for delivering an active pharmaceutical agent through the skin of the patient. The device (1) includes a body or case (2) which encompasses a microneedle array (3) (a support structure including a number of microneedles) and an actuation means (4). The body or case (2) further encompasses a controller (5) and a battery (6). Adherence to the skin can be achieved by any suitable means (7) for securing the device to the skin of the patient. Examples of suitable means (7) for securing the device to the skin of the patient include an adhesive layer (as exemplified in FIG. 1) or a belt or a rubber band.

Figure 2:
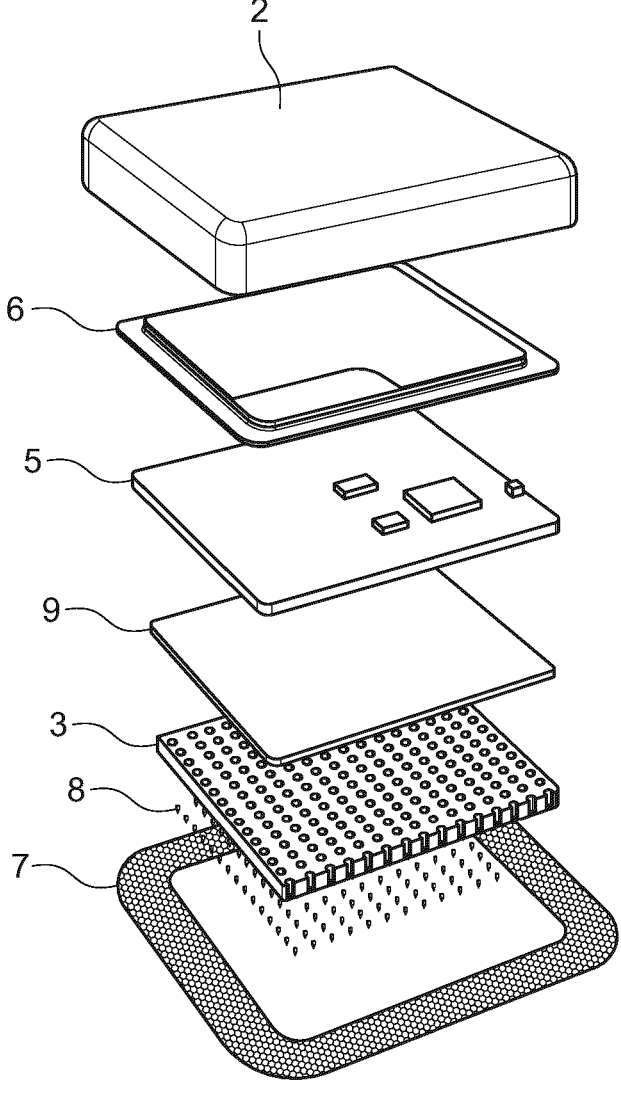
FIG. 2 shows a transdermal patch with microneedle array with a thermally expandable working medium, here a wax, as actuation means.

In FIG. 2, a more detailed structure is provided of an embodiment of the device of the invention. In such embodiment the means to actuate the microneedles (8) includes a thermally expandable working medium (9), for example a wax layer. A body or case (2) of the device encompasses a battery (6), a controller (5), a thermally expandable working medium (such as a wax layer) (9), a microneedle array (3) which microneedle array includes a number of microneedles (8). The device further includes a means (7) for securing the device onto the skin of the patient, which is suitably an adhesive layer as shown in FIG. 2.

The actuation means (4) to actuate the microneedles can be any suitable actuation means that allows penetration of the microneedles through the skin. The actuation means of the present invention is characterized therein that it allows for the actuation of each microneedle separately. Preferred means for actuation of the microneedles include the use of a thermally expandable working medium or the use of a spring and actuator pin.

Figure 4:
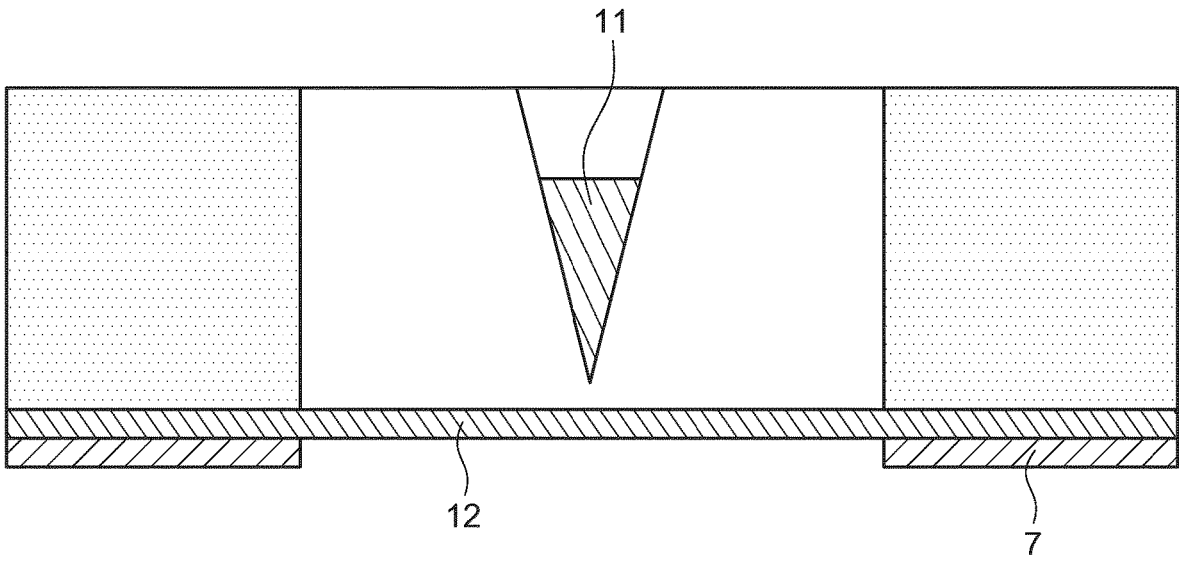
FIG. 4 shows a detailed schematic view of a needle tip and the skin contact surface.

The thermally expandable working medium can be any working medium that expands as a result of an increase in temperature. Such working medium will need to expand in such manner such as to provide a sufficient force to the microneedle. Each microneedle in the microarray is required to be able to pierce the skin and would need to be displaced to a sufficient depth for transdermal delivery of the medicament, for example subcutaneously. Considering that microneedles are commonly either coated with the medicament or the distal end of the microneedle tip contains the medicament in a biodegradable form, a microneedle is to be displaced such that the distal tip containing the medicament has traversed the skin and after actuation is located for example subcutaneously. Accordingly, where the actuation means comprises a thermally expandable medium, a suitable thermally expandable medium has a volume of expansion sufficient to exert a force of at least 1 N over the entire displacement range over which the microneedle travels. Preferably this force is of about 1 N to about 5 N. At such an expansion the resulting force has to be sufficient for the microneedle to have a stroke distance of at least 0.5 mm, suitably at least 0.65 mm, preferably of about 1 mm to about 5 mm (See FIG. 4). In FIG. 4 there is described an embodiment of a microneedle as it is included in a microneedle array. Here, prior to actuation the needle tip (11) is positioned within the device and is protected by a barrier (12) (e.g. a foil) from the exterior environment. Such barrier (12) maintains sterility of the microneedles (8) within the device. In order to maintain sterility, the environment around the microneedle is hermetically sealed through a sterile seal such as barrier (12). In certain embodiments the microneedles (8) may be individually sealed with such barrier (12). Thus, actuation of the microneedle also needs to penetrate this barrier (12) for the transdermal administration of the active pharmaceutical agent. The barrier (12) is preferably located between the microneedle array and the means (7) for adherence of the device to the skin (e.g. an adhesive layer). Considering that in FIG. 4, as an example the length of the needle tip (11) is 500 μm, the clearance between the needle tip (11) and the barrier (12) is 50 μm, and both the barrier (12) and the skin adherence means (7) having a thickness of 50 μm the minimal required stroke is at least 0.65 mm in this example.

Suitably such thermally expandable working medium is preferably a wax. Preferred waxes include for example a paraffin wax, a thermostat wax, a polyethylene glycol or a mixture thereof. Such suitable thermally expandable medium has a relative high melting point and a high thermal expansion. The high thermal expansion refers to a any paraffin or thermostat wax which upon expansion can exert a force of at least 1 N over an expansion range of 0.5 mm to 5 mm. Such as for example an expansion range in each direction in the range of 0.5 mm to 5 mm. The relative high melting point refers to paraffin waxes and thermostat waxes having a melting point which is significantly higher than the body temperature but not so high of a melting temperature which will adversely affect the other elements of the device or the patient to which the device is applied. Suitably, the melting temperature for the paraffin wax or thermostat wax is from 50° C. to 90° C., more suitably from 60° C. to 80° C., for example from 65° C. to 75° C. Suitably, the paraffin wax or thermostat wax has a narrow range of carbon chain lengths, as a wide range of carbon chain lengths for the paraffin wax or thermostat wax may result in a wide range in the melting temperature, whereas in the application for use in a device as described in this invention a defined melting temperature is more suitable. An example of a thermally expandable working medium comprises 60% hexatriacontane and 40% paraffin wax. Suitable examples of thermally expandable medium include waxes such as Kerax 1303 and Alfa 1260.

Figure 3:
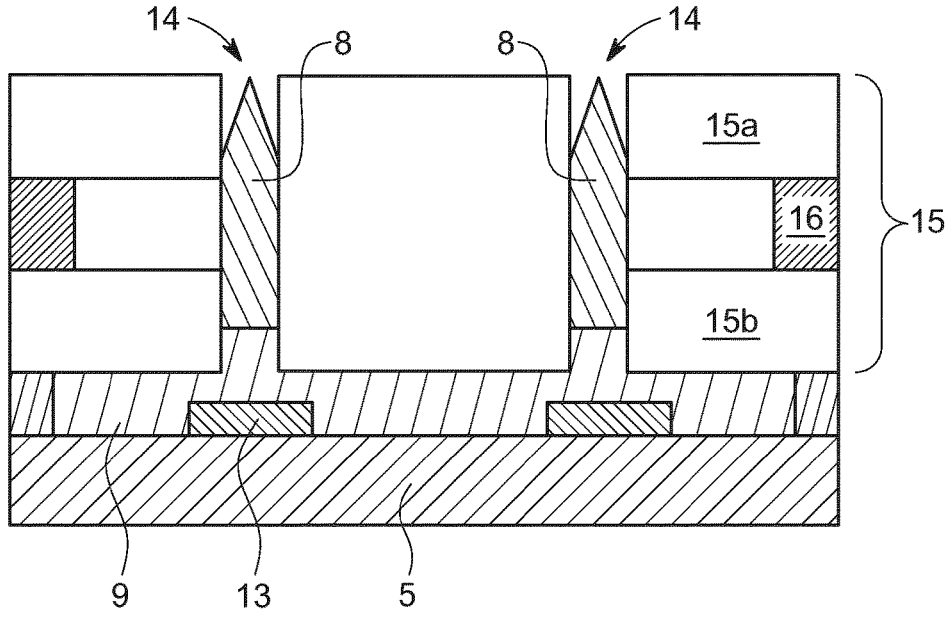
FIG. 3 shows a schematic view of a wax actuator for microneedle actuation in a microneedle array for a transdermal patch.

Such thermally expandable working medium is in close contact with a heat source (13) as shown in FIG. 3. Such heat source (13) is in direct contact with the thermally expandable working medium (9) and is regulated by the controller (5). Each microneedle (8) in the microneedle array (3) is actuated with a dedicated heat source (13). To actuate each individual microneedle (8), the heat source (13) dedicated to that microneedle produces sufficient heat to expand the thermally expandable working medium (9). In certain embodiments, such heat source (13) can be an integral part of for example a printed circuit board (PCB) included in the controller (5). In a suitable embodiment each heat source (13) is an electric heat source such as for example a resistor on a PCB.

Upon heating of the thermally expandable working medium (4) each microneedle (8) is pushed through its aperture, through the sterile barrier (12) and the patient's skin to administer a medicament. In FIG. 3 an exemplary embodiment is shown wherein the printed circuit board (PCB) includes a heat source (13) for each microneedle (8) in the microneedle array (3). The thermally expandable working medium (9) is in close contact with each heat source (13) and a controller (5) on the PCB (not shown) actuates each individual heat source to actuate each microneedle (8). Each microneedle (8) is positioned in an aperture (14). Such aperture (14) can be formed from a support plate (15). The support plate (15) can comprise one or more layers. Where the support plate (15) comprises more than one layer such layers are separated by a spacer (as shown in FIG. 3). In a preferred embodiment the support plate (15) comprises two layers (15a, 15b) separated by a spacer (16). Such spacer (16) reduces potential friction in the aperture (14), which friction may increase the required force needed to actuate the microneedles (8) for the transdermal administration of the medicament or active pharmaceutical agent.

In a suitable embodiment the microneedles (8) have a diameter of 0.3 to 0.5 mm, preferably about 0.4 mm. Microneedles suitable for application in the microneedle array of the present invention are to administer an active pharmaceutical agent/bioactive agent to the patient. As such each microneedle (8) comprises a dose or partial dose of the bioactive agent to be administered. Activation of a microneedle (8) administers the dose or partial dose to the patient. The microneedle array (4) of the delivery device of the present invention thus contains either one or more doses of the bioactive agent to be administered to the patient. Where the microneedle array (4) comprises multiple doses of the bioactive agent the controller (5) can initiate actuation of a subset of microneedles (8) to administer an appropriate dose according to a treatment regime.

The bioactive agent can be any active pharmaceutical agent as described including for example a medicament selected from a small molecule, a peptide, a protein, an antibody, a fusion protein, a DNA, and a RNA. In one embodiment the bioactive agent is a fertility medicament, such as Gonal F® (a recombinant gonadotropin). In another embodiment the bioactive agent is insulin. In yet another embodiment the bioactive agent is a cancer therapy agent. Any of such agent may be formulated into a pharmaceutical composition either as the sole active pharmaceutical ingredient or as part of combination of pharmaceutical active ingredients in the same pharmaceutical formulation.

Such pharmaceutical formulation comprising the bioactive agent is applied to the microneedles (8) in the microneedle array (3) to result in a single dose or multiple doses of the bioactive agent within the microneedle array. Application to the microneedle (8) can be in any suitable manner to have each microneedle contain a single dose or fraction of a dose of the bioactive agent. In one embodiment the microneedles (8) are solid microneedles coated with the pharmaceutical formulation containing the bioactive agent. In another embodiment, the pharmaceutical formulation containing the bioactive agent is a solid formulation with sufficient consistency and strength to form part of the microneedle (8). Suitable such solid formulation containing the bioactive agent forms part of the needle tip, i.e. the distal end of the microneedle (8), to be administered to the patient upon actuation of the microneedle. Once injected the bioactive agent is released from the formulation. In certain embodiments of the invention, the microneedles (8) of the microneedle array (4) are dissolvable microneedles, which dissolve upon contact with fluid after being actuated and injected through the patient's skin. Suitable dissolvable needles are for example described in US Patent Application No. 2017/0296465.

Figure 5:
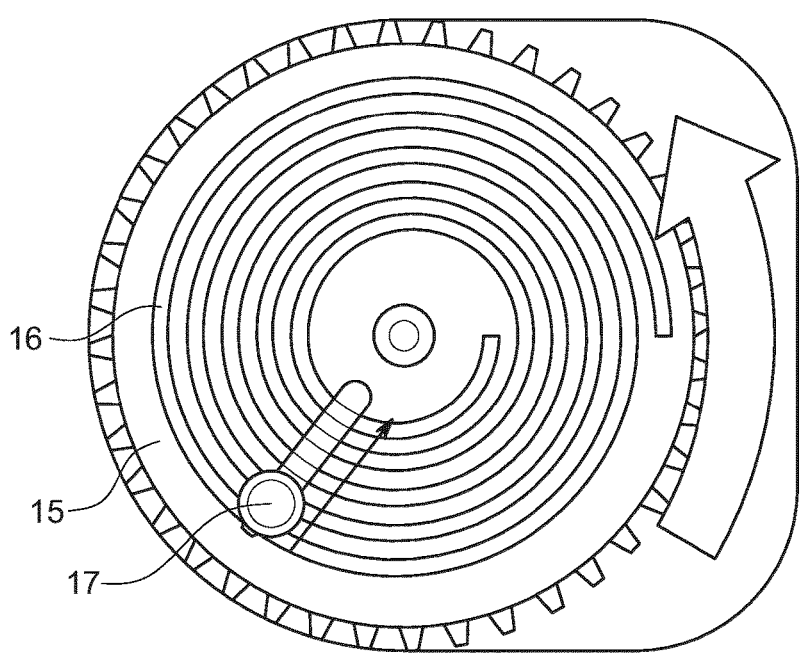
FIG. 5 shows a schematic view of a disc with a spiral-like guiding track for use as actuation in an actuator and spring mechanism.

In an alternative embodiment the actuation means (4) comprises an actuator and a spring (as shown in FIG. 5). In one such embodiment as in FIG. 5, the microneedle array (4) is arranged in a concentric arrangement. In such embodiment the actuation means (4) includes a cog wheel (15) comprising a concentric spiral track (16) on which a puck (17) is being advanced around the spiral track (16) to actuate the one or more microneedles (8). The puck (17) comprises an actuator and a spring (as shown in FIG. 6).

Figure 6A:
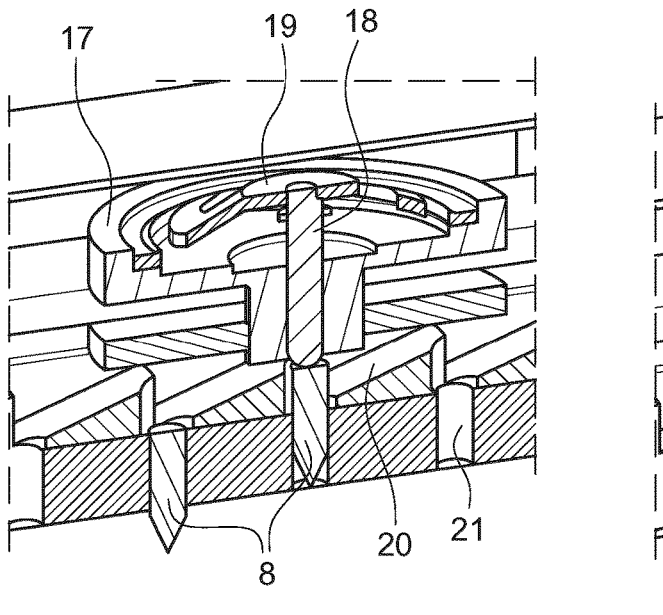
FIG. 6 shows actuation using an actuator and spring mechanism, whereas in a first step the actuator pin/puck is in an activated position pushing the needle out of the transdermal microneedle array patch (FIG. 6A), progression on an inclined slope primes the actuator pin/puck for pushing a subsequent needle out of the transdermal microneedle array patch (FIG. 6B).
Figure 6B:
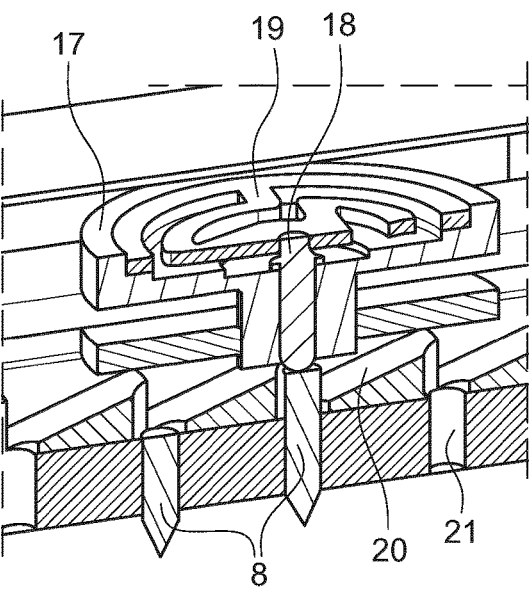

Advancement around the spiral track (16) of the puck (17) successively actuates the one or more microneedles (8) to be actuated for delivering a dose. As shown in FIGS. 6A and 6B the puck (17) comprises actuator (18) and a spring (19). The spiral track (16) comprises successive inclines, each incline (20) immediately followed by a hole (21) prior to the next incline (20). Advancement of the puck (17) along the incline (20) pushes up the actuator (18) against the spring (19) thereby creating spring force potential (as shown in FIG. 6A). Further advancement of the puck (17) over the hole releases the spring force potential and activates the spring (19) to actuate the actuator (18) to push down on the microneedle (8) (as shown in FIG. 6B) with sufficient force to penetrate both the sterile barrier (12) and the skin of the patient (not shown here). Advancement of the puck (17) along the spiral track repeats this cycle of priming the spring (19) with a spring force potential and releasing the spring (19) to actuate the actuator (18) to push down the microneedle (8) to administer the bioactive agent to the patient. The spring (19) can be any shaped spring capable of releasing the spring force potential onto the actuator (18). Such spring (19) suitably is a spring having K values in the range of about 0.01 N/mm to about 10 N/mm. Suitably the spring has a K value of 1 N/mm.

Figure 7A:
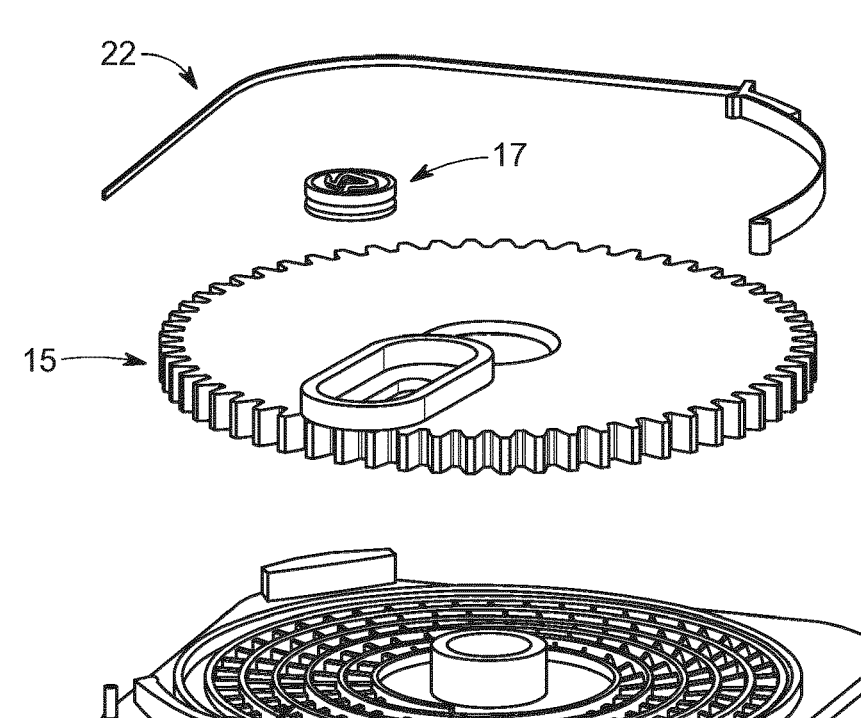
FIG. 7 shows mechanisms to advance the pin/puck over successive microneedles in the microneedle array, in a first mechanism a SMA (shape memory alloy) spring is used to advance a rotating disc incrementally to the next increment (FIG. 7A), in a second mechanism a rotating disc is advanced incrementally using a rotating spindle (FIG. 7B).
Figure 7B:
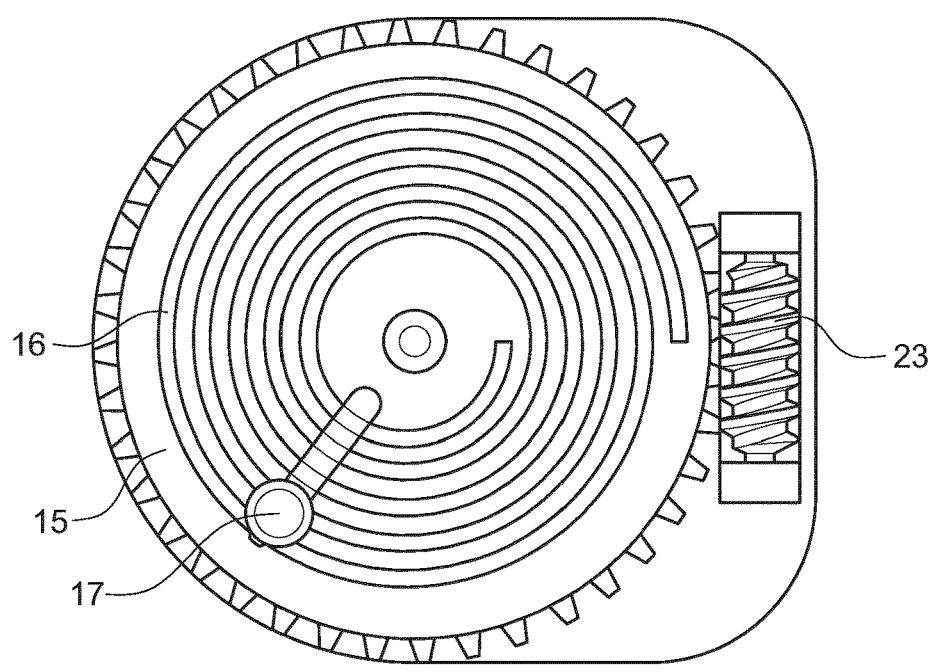

The puck (17) may be advanced around the spiral track (16) in any suitable manner. FIGS. 7A and 7B provide examples of alternative mechanisms for advancing the puck (17) around the spiral track (16). In both examples the spiral track (16) is stationary while the puck (17) is slidably connected with a cog wheel (15). Rotation of the cog wheel (15) results advancing the puck (17) around the spiral track (16). Such advancement of the puck (17) is incremental based on the number of microneedles (8) is intended to be injected for each dose. The incremental advancement of the puck (17) around the spiral track (16) is controlled by the incremental rotation of the cog wheel (15). The rotation of the cog wheel (15) is carried out using the action of for example a shape memory alloy (SMA) spring (22) as is shown in FIG. 7A. In another example (FIG. 7B) rotation of the cog wheel (15) is carried out using a spindle (23). Rotation of the spindle (23) through an external force in incremental steps results in the rotation of the cog wheel (15). The external force can be provided by any force which will rotate the spindle (23), such as for example a step motor or a brushless motor.

Whether actuation of the microneedles is carried out using a wax motor or the movement of a puck around a spiral track, the number of microneedles (8) to be injected is preset based on the dosing regimen for the particular bioactive agent. The controller (5) in the device actuates the preset number of microneedles (8) based on the dosing regimen at one or more preset times during the treatment period. The controller (5) can be configured with a preset schedule for dosing the bioactive agent, such as for example in a step of initiating the device when or immediately before the device is placed on the patient. The dose (i.e. the number of microneedles (8) to be injected) can also be adjusted over time by adjusting the configuration of the controller (5) after having placed the device on the patient. The controller (5) can be configured either directly on the device (for example through a user interface) or remotely. The controller (5) suitably comprises a processing module as well as a communication module. Such communication module can be connected to an external server through any suitable means, such as for example a fixed connection or through a wireless connection. In such device wherein the controller (5) is connected to a remote server adjustment of the dose can be carried out remotely through the communication module of the controller (5) and after remote adjustment, the controller (5) can be configured with an adjusted dosing regimen.

In addition, the controller (5) may further include a processing module for storing injection or usage date. Connection through the communication module in controller (5), with a central or external server allows for the collection of usage and injection data. Usage and injection data can be processed on the external server to provide additional information to the health care professional or to the patient to monitor or correlate any patient outcomes with adherence to a certain dosing regimen. It is understood that the data using the communication module in controller (5) can be send by wireless connection through any cloud services or through a dedicated App.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

The invention claimed is:

1. A device for delivery of a bioactive agent through mammalian skin comprising an array of microneedles and a means to actuate the microneedles, wherein the actuation means actuates the microneedles separately, and wherein the actuation means further comprises a spiral track on which the actuator is moved from one microneedle to the next microneedle.

2. The device according to claim 1, wherein the actuation means actuates of a subset of the array of microneedles at the same time, the subset comprising 2 or more microneedles.

3. The device according to claim 2, wherein actuation of a subset of the array of microneedles at the same time comprises actuation over a period of 1 to 60 sec.

4. The device according to claim 1, wherein the device is an on-skin device further comprising a means for adhering to mammalian skin, wherein the means for adhering to the skin is selected from an adhesive, a belt and a rubber band.

5. The device according to claim 1, wherein the microneedles comprise the bioactive agent.

6. The device according to claim 5, wherein the microneedle is coated with the bioactive agent.

7. The device according to claim 5, wherein at least a portion of the distal end of the microneedle is a solid formulation comprising the bioactive agent.

8. The device according to claim 1, wherein the bioactive agent is a medicament selected from a small molecule, a peptide, a protein, an antibody, a fusion protein, a DNA, an RNA, a fertility medicant, insulin and a cancer therapy agent.

9. The device according to claim 1, wherein the microneedles dissolve in contact with fluid after actuation of the microneedle thereby releasing the bioactive agent to the mammal.

10. The device according to claim 1, wherein the actuation means comprises an actuator and a thermally expandable working medium.

11. The device according to claim 1, wherein the actuation means further comprises a heat source.

12. The device according to claim 1, wherein each microneedle in the array is coupled with a separate heat source.

13. The device according to claim 1, wherein the actuation means comprises an actuator and a spring, and the actuation means further comprises a cog wheel comprising a concentric spiral track on which a puck is being advanced around the spiral track to actuate one or more microneedles.

14. The device according to claim 13, wherein the spring is primed repeatedly prior to engagement of the actuator with each separate microneedle.

15. The device according to claim 13, wherein the spiral track comprises successive inclines, each incline immediately followed by a hole prior to a next incline, and advancement of the puck over the hole releases spring force potential and activates the spring to actuate the actuator to push down on the microneedle.

16. The device according to claim 1, wherein the microneedles are actuated at a force of at least 0.5 N and an actuation stroke of at least 0.5 mm.

17. The device according to claim 1, wherein the time period between each actuation is controllable.

18. A method of administering a bioactive agent to a mammal using the device according to claim 1.

19. The method according to claim 18, wherein mammal is a human.

20. The method according to claim 19, wherein the bioactive agent is selected from a fertility medicament, insulin and a cancer treatment.

\* \* \* \* \*